United States Patent [19]

Bernard et al.

[11] Patent Number: 5,639,654
[45] Date of Patent: Jun. 17, 1997

[54] PROCESS FOR CREATING A SKIN SUBSTITUTE AND THE RESULTING SKIN SUBSTITUTE

[75] Inventors: Bruno Bernard, Antibes; Maris-Cécile Lenoir, Valbonne; Braham Shroot; Yves-Michel Darmon, both of Antibes; Daniel Asselineau, Valbonne, all of France

[73] Assignee: Centre International de Recherches Dermatologiques, Valbame, France

[21] Appl. No.: 470,959

[22] Filed: Jun. 6, 1995

Related U.S. Application Data

[63] Continuation of Ser. No. 625,053, Dec. 10, 1990, abandoned, which is a continuation of Ser. No. 166,097, Mar. 9, 1988, abandoned.

[30] Foreign Application Priority Data

Mar. 26, 1987 [FR] France ................... 87 04205

[51] Int. Cl.⁶ .................... C12N 5/06; A61F 2/10
[52] U.S. Cl. .................... 435/325; 435/378; 435/70.1; 435/1.1; 435/395; 435/347; 623/15; 606/132; 602/42; 602/43; 602/44; 602/45; 602/46; 424/78.06; 424/574
[58] Field of Search ............... 623/15; 606/132; 424/78.06; 602/42, 43, 44, 45, 46; 435/1.1, 240.2, 70.1, 240.21, 240.23

[56] References Cited

U.S. PATENT DOCUMENTS

| 4,485,096 | 11/1984 | Bell | ......... 424/532 |
| 4,604,346 | 8/1986 | Bell | ......... 606/132 |

FOREIGN PATENT DOCUMENTS 8602273  4/1986  WIPO.

OTHER PUBLICATIONS

Limat et al, J. Invest. Dermatol., 87, 1986 pp. 485–488.
Vermorken, A. J. M. 1985 Atla 13, 8–37.

*Primary Examiner*—Christopher S. F. Low
*Attorney, Agent, or Firm*—Cushman Darby & Cushman IP Group of Pillsbury Madison & Sutro LLP

[57] ABSTRACT

The invention concerns a process for obtaining a skin substitute and the skin substitute itself. According to this process, a dermis substitute is prepared by mixing contractile cells, a nutritive medium, and collagen, in order to form a contracting gel; this dermis substitute is used as a substrate for an epidermis substitute obtained by culturing, using keratinocytes from an animal or human skin sample. According to the invention, the substrate is implanted with at least one section of a hair follicle retaining at least partially its cellular sheath, this section being implanted perpendicularly to the free surface of the substrate.

21 Claims, 2 Drawing Sheets

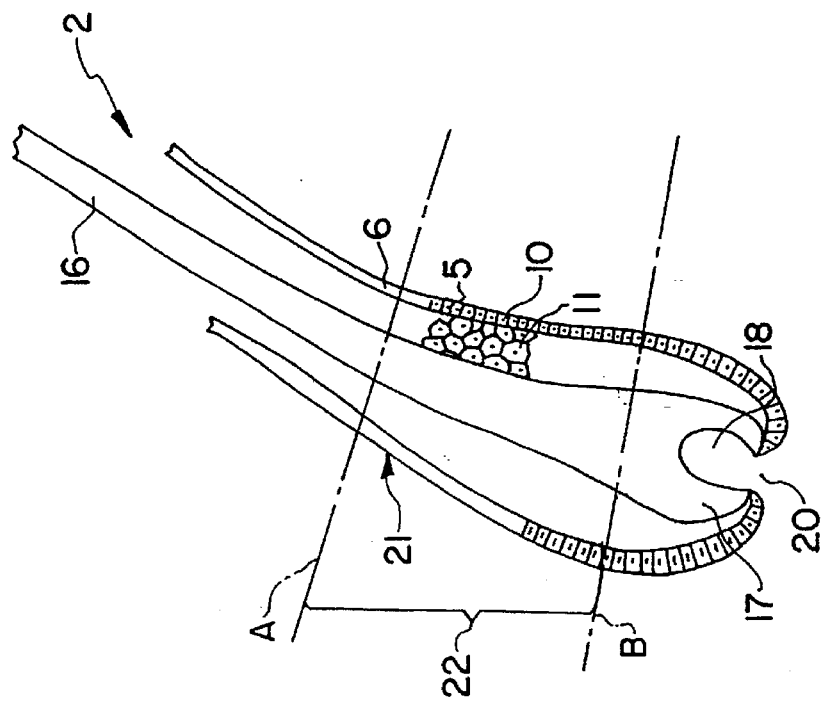
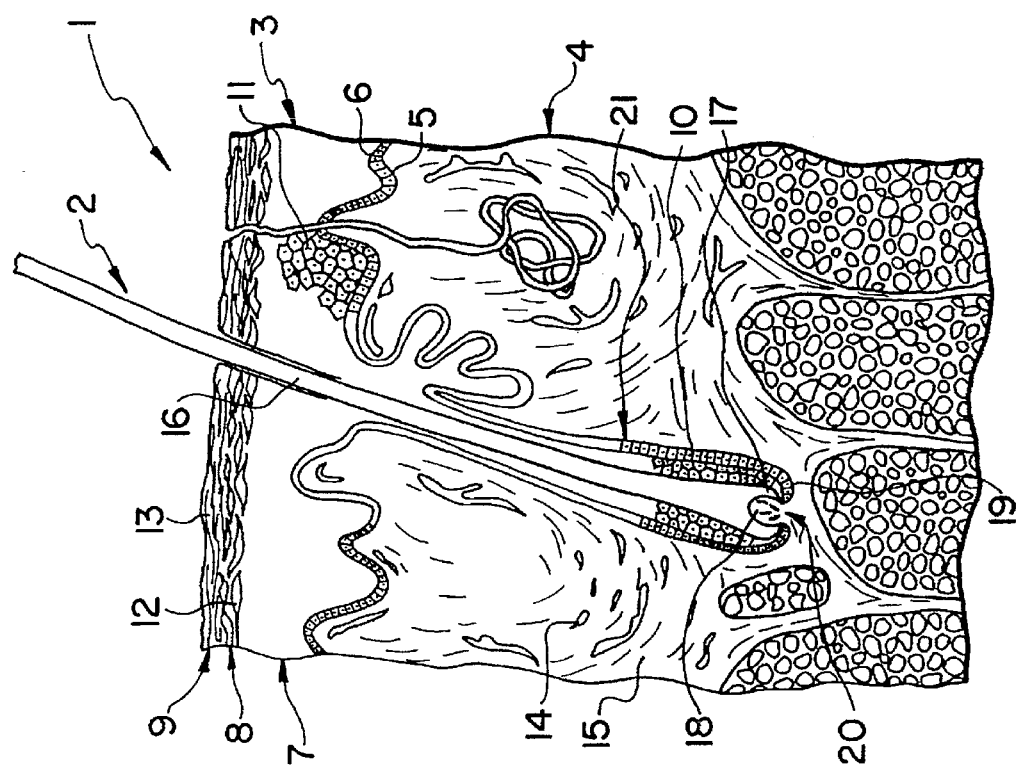
FIG. 1
FIG. 2

PROCESS FOR CREATING A SKIN SUBSTITUTE AND THE RESULTING SKIN SUBSTITUTE

This is a continuation of application Ser. No. 07/625,053, filed Dec. 10, 1990, now abandoned which is a continuation of application Ser. No. 07/166,097 filed Mar. 9, 1988, now abandoned.

The invention concerns the process for obtaining a skin substitute, and the skin substitute thus created.

As is well known, research is being undertaken to create in vitro cellular structures comparable to animal or human skin. These structures could be used, in particular, in gifts for injured persons such as severe burn victims. The structures sought by researchers should, of course, possess similarities as pronounced as possible with the structure of human skin, in order to avoid the risk of graft rejection. In addition, it would be possible to use a material of this nature to study the effects produced by various pharmacological or cosmetic products; the results of such studies would increase in reliability as the similarities between the skin substitute and skin itself became stronger.

It is, therefore, intended that the invention describe a process for creating a skin substitute possessing more significant similarities with real skin than those now existing in materials of this kind currently known.

The capacity of keratinocytes to be cultured in a suitable nutritive medium is well known. More specifically, F. K. Noser's article, published in "The Journal of Investigative Dermatology" (87, 485–488, 1986), demonstrates the culturing capacity of keratinocytes taken from the sheath of a human hair follicle. Furthermore, the article of A. J. M. Vermorken, published in "Molec. Biol. Rep." (10, 205–213, 1985), demonstrates that culturing of keratinocytes from the sheath of a hair follicle may lead to formation of a cellular layer composed of a multiplicity of sub-layers exhibiting differentiation, in a way that is somewhat similar to the structure observed in animal or human skin. It has been suggested that the formation of this cellular layer might be achieved by using a known type of skin substitute as base material. However, no more precise information has been provided in this regard. Moreover, immersion cultures, which have been described, produce a cellular layer structure that still exhibits perceptible differences with the structure of animal or human skin.

The international PCT application, published as #WO 86/02273, describes a process for the creation of a skin substitute which uses the culturing capacity of keratinocytes; skin biopsies are used as sources of the keratinocytes. Following this process, researchers, using a soft acid extraction process applied to a source such as rat tail tendons, obtain type I collagen that is then kept in solution in a slightly acidic environment. In addition, using sources such as human tissue, fibroblasts are grown in a culture medium. The collagen solution is neutralized with a base, and nutritive substances are added. Next, the fibroblasts are added. The result is the formation of a gel which contracts due to interactions between the fibroblasts and the collagen molecules, the expulsion of the nutritive medium, and, finally, the formation of the skin substitute. Before contraction of the gel, a skin biopsy, approximately 2 mm in diameter, is inserted and positioned so that the epidermis of the biopsy lightly touches the gel surface. A migration and proliferation of keratinocytes from the biopsy is then observed at the surface of the skin substitute. The phases of differentiation of the keratinocytes ultimately lead to the formation of the different layers of the skin substitute.

Problems are, however, associated with a process of this kind. For example, the skin substitute thus produced is not uniform over its entire surface, since the biopsy, including the dermal portion, remains inserted in the dermis substitute. Another disadvantage lies in the manner in which the biopsy is taken: the procedure must be carried out by a doctor, it may be painful, and my leave visible scars. Furthermore, the risk that the handler may be contaminated by infectious agents, is significant. Lastly, the surface-area of the skin substitute obtained is limited by the number of biopsies that may be taken from a single person.

The procedure specified by the invention avoids these problems, since it uses, in a specified and original way, the culturing capacity of the keratinocytes contained in the sheath of a hair follicle. As specified by the invention, the biopsy used according to document #WO 86/02273 is replaced by a hair follicle enclosed in its sheath, which is implanted in a distinctly perpendicular position in the free surface of the dermis substitute being formed. Specialists are completely surprised by the resulting differentiation of the keratinocytes, which form what is, in fact, an epidermis substitute having completely unexpected similarities to human skin. Thus, although the keratinocytes constitute the source of the formation of an epidermis substitute, according to both the document #WO 86/02273 and the invention process, the insertion of a hair follicle perpendicular to the free surface of the dermis substitute in the process of formation, is not the equivalent of inserting a skin biopsy, as far as results are concerned; this latter process improves results noticeably. In addition, the structure of the cellular layer, which constitutes the final epidermis substitute, exhibits more significant similarities with the structure of skin then does the cellular layer that had been formed by culturing in a different way the same cells taken from the sheath of a hair follicle (article of A. J. M. Vermorken previously mentioned). Finally, the bonding between the layers made up of the dermis and epidermis substitutes is satisfactory and permits easy handling of the skin equivalent.

The skin substitute produced in this way, according to invention specifications, is well differentiated and structured. It is also impermeable and homogeneous over its entire surface. As a matter of fact, if, during the process, one were to remove the hair follicle(s) from the dermis substitute, the hole(s) thus created in the skin substitute would close up.

The differentiation achieved in vitro by following the invention process resembles very closely what is observed in vivo. In particular, the filaggrine in the granular layer of the epidermis can be detected, as in normal skin; using electrophoresis, it may be observed that the filaggrine has been obtained by cutting the profilaggrine in the oligopeptide bonds. Furthermore, a palisade arrangement of the basal cells is evident; this is mainly the result of the insertion of hair follicles perpendicularly to the surface of the dermis substitute in its developmental stage.

Implantation of the hair follicle gives the skin substitute a surface that is of the same perceptible size as the sun, ace obtained using a biopsy. However, a very large surface-area may be obtained using a large number of follicles from a single donor, which is impossible using the biopsy method.

The skin substitute thus obtained may be used, most notably, in grafts for the treatment of wounds. In this case, the donor and the recipient may both be: humans, and the hair-follicle donor may, in fact, be the recipient of the skin substitute.

The invention thus concerns, first, a process for obtaining a skin substitute in which:

(1) a dermis substitute is prepared by mixing:
   a. contractile cells gathered, for example, from unilayer cultures groom in a nutritive medium using fragments of human or animal tissue; and
   b. a nutritive medium (MN 1) to which are added components of the extracellular matrix of the dermis.

This mixture forms a gel which contracts, expelling the nutritive medium as it forms the dermis substitute.

(2) the dermis substitute obtained in paragraph (1) above is used as a substrate for an epidermis substitute obtained from culturing this substrate with keratinocytes from an extracted animal or human sample, and from the maintenance of conditions promoting the proliferation of keratinocytes on the surface of the substrate. The growth of the keratinocyte culture is promoted by the use of at least one medium (MN 1, MN 2) in contact with the keratinocytes. The process is further characterized by the fact that the substrate is cultured using at least one hair follicle or a section of hair follicle extracted from human or animal skin; this follicle or follicle section, still surrounded by at least a portion of its cellular sheath, is implanted in the substrate in such a way that the median longitudinal line is perceptibly perpendicular to the free surface of the substrate.

Fibroblasts my be used as contractile cells; for optimal results, it is best to use, as contractile cells, dermal fibroblasts obtained from healthy human donors and collected from unilayer cultures by means of careful trypsinization.

The preferred nutritive medium for contractile cell cultures is the Essential Minimum Medium. The optimal medium for cultures containing components of the extracellular matrix of the dermis, contains at least some quantity of collagen, especially of type I.

Using one preferred method of production, the dermis substitute is prepared by following these steps:

a. A slightly acidic collagen solution is obtained by soft acid extraction from an animal or human source. This collagen may also be obtained commercially, as, for example, the product sold by the Bioetica company.

b. The solution obtained in step (a) is mixed with contractile cells and a nutritive medium (MN 1). A base is added to neutralize the mixture, which is then poured into a flat receptacle.

c. The gel thus obtained is allowed to contract for several days.

The following preferred formula is used for the nutritive medium (MN 1):

80–100% by volume of an Essential Minimum Medium;
0–20% by volume of fetal calf serum;
0–20% by volume of human type AB serum;
0–1% by weight of anti-fungal agent(s);
0–10% by weight of antibiotic(s);
0–2% by weight of energizing compound(s);
0–2% by weight of non-essential amino acids.

The implant may be set into the substrate a distance of between 0.1 and 2 mm, measured from the free surface of the substrate. The preferred method of obtaining the implant is to cut the extracted hair follicle perpendicularly to its median longitudinal line, in the area in which the follicle is enclosed in its cellular sheath in order to preserve a follicle length of approximately 0.5–5 mm. It is best to cut the follicle near the base in order to eliminate the bulb. The implant should be inserted into the substrate at the beginning of the contraction of the gel, which constitutes the substrate.

It is best, following culturing of the substrate, to keep the implanted substrate immersed in a nutritive medium for a specific period of time $T_1$. The nutritive medium (MN 1) should cover the implant(s). A time-period $T_1$ of about 5 or 6 days my be chosen.

When the time-period $T_1$ expires, the medium (MN 1) should be replaced with a medium (MN 2) that should reach a level located within the thickness of the dermis substitute. In order to ensure that the medium (MN 2) reaches the desired level, the dermis substitute should be placed on a support-grid raised of the receptacle bottom. The level of the medium (MN 2) should he adjusted until the support-grid is barely covered, without, however, covering the upper surface of the skin substitute being formed.

The following formula for the medium (MN 2) my be used:

80–100% by volume of Essential Minimum Medium;
0–10% by weight of antibiotic(s) and/or anti-fungal agent(s);
0–20% by volume of animal or human serum;
0–0.5% by weight of growth factor(s).

The implant should be extracted from the substrate at the end of time-period $T_2$ after implantation. The time-period $T_2$ may be from 8 to 13 days, and the skin substitute may be kept in contact with the culture medium until expiration of time-period $T_3$ after insertion in the dermis substitute. The time-period $T_3$ should exceed time-period $T_2$, thus permitting the keratinocytes developed on the substrate to totally cover the substrate, with significant differentiation of the keratinocytes.

The substrate my be cultured using implants evenly arranged and spaced approximately 0.5 to 2.5 cm apart. A time-period $T_3$ of from 15 days to several months should be chosen.

The invention also concerns a skin substitute made up of a dermis substitute covered with an epidermis substitute. The dermis substitute is a film composed of a type I collagen gel containing fibroblasts arranged three-dimensionally in the film. The skin substitute is also characterized by the fact that the epidermis substitute contains:

a. a basal membrane equivalent made up of the deposit of a layer of laminine, fibronectin, type IV collagen, and bubbly pemphigus antigen;

b. basal layer cells in a palisade arrangement attached to the membrane substitute in paragraph (a) by hemidesmosomes;

c. cells from the suprabasal layers which, beginning in the first suprabasal layer, contain basic keratin having a value of 67 kDa and acidic keratin with a value of 56.5 kDa;

d. granular cells containing grains of keratohyalin, involucrine, transglutaminase, and filaggrine;

e. flat, keratinized cells arranged near the free surface and producing, after extraction with dodecyl sodium sulfate and 2-mercaptoethanol, corneous envelopes which are characteristic of corneocytes. The cells of the various layers are attached to each other by desmosomes.

Finally, the invention concerns a skin substitute characterized by the fact that it is formed according to the process described above.

In order to increase understanding of the purpose of the invention, a description will be offered below, as a purely illustrative and non-limiting example, of one particular way in which the invention may be used, as represented in the attached drawings. In these drawings:

FIG. 1 is a partial section of a skin sample (from the scalp), in which a hair follicle is implanted;

FIG. 2 represents the hair mentioned in FIG. 1 after extraction from the scalp sample;

Figure 3:
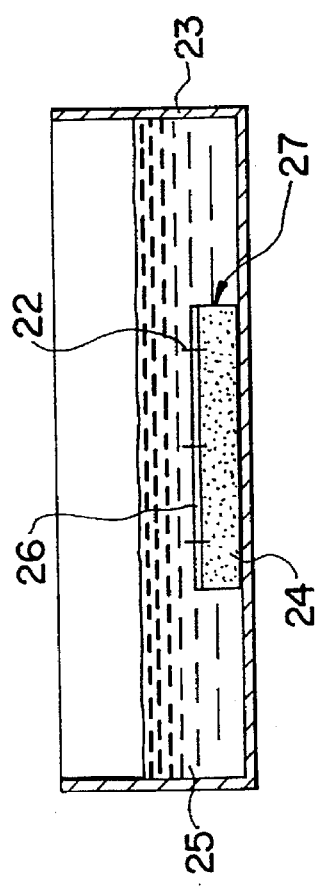
FIG. 3 shows a skin substitute being formed, immersed in a nutritive medium.

FIG. 1 shows a skin sample taken from the scalp, indicated in its entirety by the number 1, in which a hair follicle (2) is implanted. The follicle develops in the epidermis, indicated in its entirety by (3). The epidermis is separated from the dermis (4) by a basal membrane (5). Within the epidermis, four layers may be distinguished: beginning with the basal membrane towards the skin surface, they are the basal layer (6), the Malpighian layer (7), the granular layer (8), and the corneous layer (9).

95% of the epidermis is composed of cells called keratinocytes, which exhibit differentiation from the basal to the corneous layers. The basal layer(6) is made up of a single layer of keratinocytes (10) having a distinctly parallelepiped shape. These cells are structured on a main axis clearly perpendicular to the basal membrane (5), and are attached to this membrane at their base by means of hemidesmosomes (39). The Malpighian layer (7) is composed basically of a stacking of layers of polyhedral keratinocytes (11). Between the Malpighian layer (7) and the corneous layer (9) are found two or three flat keratinocyte layers (12) making up the granular layer (8). Finally, the corneous layer (9) is composed of a stacking of cells distinctly hexagonal in shape (13), dead, flat, and evenly arranged, The dermis (4) contains fibroblasts (14) bathed in an extracellular matrix (15), composed, in turn, of macromolecules such as collagens, mucopolysaccharides, glycoaminoglycans, or fibronectin.

The hair (2) is made up of the body (16), of which the portion implanted in the epidermis terminates in a bulb (17). At the base of the bulb (17) is found a cavity (18) containing dermal papillae (19); the cavity opens onto the dermis through an orifice (20). One portion of the basal membrane (5) of the epidermis partially encloses the body (16) of the hair (2) as well as the bulb (17), and is attached to the bulb while the orifice (20) is kept open. This portion of the basal membrane constitutes, in this way, a sheath (21) bordered on the exterior face by keratinocytes (10) of the basal layer; the sheath encloses, between this layer and the hair, polyhedral keratinocytes (11) in the Malpighian layer.

During one stage of the process, an implant, made up of a portion of the hair (2) is prepared, as follows: the hair is easily and painlessly extracted without risk of infection, be means of tongs. This procedure requires no medical expertise. A hair extracted in this way is shown in FIG. 2.

During extraction of the implant, the sheath (21) separates from the basal layer surrounding it by rupture of the layer. Two eventualities may occur at this point: either, during extraction, the basal layer breaks at the bulb and only the body (16) of the hair is extracted, in which case the sheath remains in the epidermis; or the basal membrane breaks above the bulb, in particular at the point where the dermis and epidermis meet, in which case a hair is extracted, of which the lower part is enclosed in the sheath (21). Only this second eventuality is practiced during the implant preparation stage; hairs extracted without a sheath are not used. If dermal papillae remain in the epidermis (3) during extraction, the extracted hair (2) contains neither fibroblasts nor any dermal contaminant whatsoever; these last two are, in fact, problem-causing elements in a culture. Furthermore, the dermal papillae may produce regrowth of a hair and reformation of a sheath (21) containing keratinocytes (10 and 11). The hair follicle represents, therefore, an almost limitless source of keratinocytes.

The extracted hair is cut perpendicularly to its median longitudinal line, in the area in which it is enclosed in its sheath (21), at locations A and B in FIG. 2: B is located above the bulb, and A above B, in order to maintain an AB segment between 0.5 and 5 mm in length.

The bulb (17) is thus cut off, since, on the one hand, the soft extremity may prove troublesome in further stages of the process, as explained below; on the other hand, all risk of contamination from dermal papillae that may have remained attached to the bulb, is eliminated. The impant thus obtained (22) is ready for use.

At the same time that the implant (22) is being prepared, another stage of the process is under way, consisting of the prearation of a structure equivalent to the dermis (4), that will be termed the dermis substitute. This preparation is carried out, according to known procedures, as indicated below.

Fragments of cutaneous tissue including dermis and epidermis are taken from human donors. The fragments are then arranged in a dish placed in a culture medium, the "Essential Minimum Medium," which is sold, for example, by the Seromed Company, and for which the conventional composition is given in Table I below.

TABLE I

| ESSENTIAL MINIMUM MEDIUM | |
|---|---|
| CONSTITUENT ELEMENTS | QUANTITIES IN MG/L |
| NaCl | 6800 |
| KCl | 400 |
| $Na_2HPO_4.2H_2O$ | — |
| $NaH_2pO_4.H_2O$ | 140 |
| $KH_2PO_4$ | — |
| $MgSO_4.7H_2O$ | 200 |
| $CaCl_2$ | 200 |
| D-Glucose | 1000 |
| Red Phenol | 10 |
| $NaHCO_3$ | 2200 |
| L-Arginine.HCl | 126 |
| L-Cystine | 24 |
| L-Glutamine | 292 |
| L-Histidine | 42 |
| L-Isoleucine | 52 |
| L-Leucine | 52 |
| L-Lysine.HCl | 73 |
| L-Methionine | 15 |
| L-Phenylalanine | 32 |
| L-Threonine | 48 |
| L-Tryptophan | 10 |
| L-Tyrosine | 36 |
| L-Valine | 46 |
| D-Ca-Pantothenate | 1 |
| Pyridoxal.HCl | 1 |
| Thiamine | 1 |
| Riboflavin | 0.1 |
| i-Inositol | 2 |
| Folic Acid | 1 |
| Choline Chloride | 1 |
| Nicotinamide | 1 |

The dermal fibroblasts then tolerate out of the cutaneous tissue and proliferate in a single layer on the bottom of the container.

Next, a slightly acidic type I collagen solution is prepared. The collagen has already been obtained by soft acid extraction from rat tail tendons.

The slightly acidic collagen solution is then mixed with fibroblasts that have been cultured in a single byes, as described above, and collected by careful trypsinization from confluent or subconfluent cultures, in contact with a nutritive medium (MN 1) having the following composition:
- 85–90% by volume of Essential Minimum Medium;
- 10% by volume of fetal calf serum, or 10% by volume of human AB serum;
- 1% by weight of non-essential amino acids (as shown in Table II below).

TABLE II

NON ESSENTIAL AMINO ACIDS

| CONSTITUENT ELEMENTS | QUANTITIES IN MG/L |
|---|---|
| L-Alanine | 8.90 |
| L-Asparagine.H$_2$O | 15.00 |
| L-Aspartic acid | 13.30 |
| L-Gutamic acid | 14.70 |
| L-Glycine | 7.50 |
| L-Proline | 11.50 |
| L-Serine | 10.50 |

100 U/ml of penicillin
100 g/ml of streptomycin
2.5 g/ml of amphotericin B
1 mM of sodium pyruvate The mixture is neutralized using soda 0.1N, and poured into a flat container (23) as shown in FIG. 3. The mixture solidifies very rapidly into a gel.

As a result of the interactions between the fibroblasts, which are contractile cells, and the collagen fibers contained in the nutritive medium made into a gel, the gel volume diminishes, the nutritive medium is expelled, and a dermis equivalent forms. The contraction of the gel is allowed to continue for several days; during that time, the gel volume is reduced by a factor of at least twenty.

The fibroblasts are not the only contractile cells that may be used. Among other cells that may be used, for example, are striated- and smooth-muscle cells, heart-muscle cells, and blood platelets.

Similarly, although, in the preceding example, a type I collagen solution as used as a component of the extracellular dermal matrix, other types of collagens are suitable for use in the formation of the dermis substitute. It is recommended that these collagen types be composed of complete molecules that have retained their telopeptides. Type I collagen belongs to this group, but mention could also be made of human collagen extracted from the placenta following partial enzymatic digestion.

After preparation of the gel which forms the dermis equivalent (24), the next stage of the process is begun: the creation of the epidermis using the dermis substitute.

The implant (22), obtained as specified above, is inserted into the gel during the first minutes of gel contraction, in such a way that its median longitudinal line extends perpendicularly from the free surface of the gel. At this stage of the implant (22) insertion, the follicle bulb may cause difficulties, since the soft portion does not facilitate insertion into the gel. For this reason, it is recommended that the bulb be cut off during preparation of the implant.

During the gel-contraction phase, during which the dermis substitute (24) is formed, the implant (22) is held solidly in place in the gel. FIG. 3 shows a dermis substitute (24) in which several implants have been inserted. It is, in fact, possible to prepare the dermis substitute, during its formative stage, using implants evenly arranged and spaced approximately 0.5 to 2.5 cm apart. After implant insertion, the dermis substitute (24) is kept immersed in the nutritive medium (MN 1) (25) for 5–6 days. This culture medium (25) covers the implants as shown in FIG. 3. During this phase, proliferation begins of the keratinocytes in the follicle sheaths (21). One may observe, at this point, a radial and vertical movement of the keratinocytes begining in the implants and extending toward the surface of the dermis substitute (2).

The migration of keratinocytes will lead to the formation of an epidermis substitute (26) on top of the dermis substitute.

Taken together, the dermis substitute (24) and the epidermis substitute (26) will make up the skin substitute (27).

At the end of this 5–6-day period, the medium (MN 1) is replaced by the medium (MN 2) (29) composed as follows:
- 85–90% by volume of Essential Minimum Medium;
- 0–10% by weight of antibiotics (penicillin, streptomycin, amphotericin B);
- 10% by volume of animal or human serum;
- 0–0.5% by volume of growth factors (epidermal growth factor, hydrocortisone, choleraix toxin).

Figure 4:
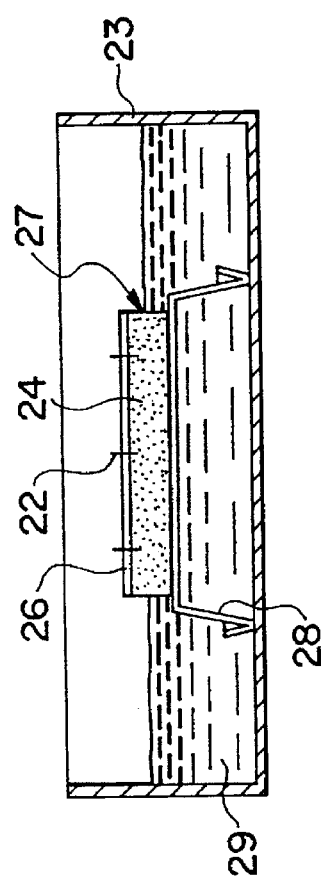
FIG. 4 shows the skin substitute represented in FIG. 3 in contact with air, during a later phase of formation.

At the same time, the skin substitute (27) is placed on a stainless-steel grid (28) set on the bottom of the container (23). This grid keeps the skin substitute raised in the culture dish (23) near the meeting point of air and liquid, as shown in FIG. 4. The medium (MN 2) level is adjusted so that the support-grid (28) is barely covered, but without covering the upper surface of the skin substitute (27) in the process of formation. The placement of the developing skin substitute in contact with air and the maintenance of the nourishment of the keratinocytes by the dermis substitute promotes the differentiation of the keratinocytes and, therefore, the formation of a properly structured skin substitute.

After 8–13 days, the implants are removed, and the developing epidermis substitute remains positioned over the dermis substitute. Given the small diameter of the implants (approximately 0.5 mm), the holes left by the extraction of the implants from the skin substitute close up, leaving a skin substitute that is uniform over its entire surface, without holes, and impermeable.

After extraction of the implants (22), the skin equivalent (27) is kept in contact with the medium (MN 2) for a time-period that permits the keratinocytes developed on the dermis substitute to cover completely this substitute. The growth of the epidermis substitute is measured by coloring the epithelial covering with Nile blue stain in a water solution of 1/10,000, and by measuring the surface of the epidermis substitute.

The surface of the skin substitute (27) varies as a function of the number of implants inserted in the dermis substitute and of the surface-area of that substitute. Thus, using a simple implant having a diameter of approximately 0.5 mm, a skin substitute is obtained after 10–12 days having a surface-area of about 1 cm$^2$. It is, of course, possible to obtain a larger surface-area by insertion into the dermis substitute of implants evenly arranged and spaced approximately 0.5 to 2.5 cm apart.

Figure 5:
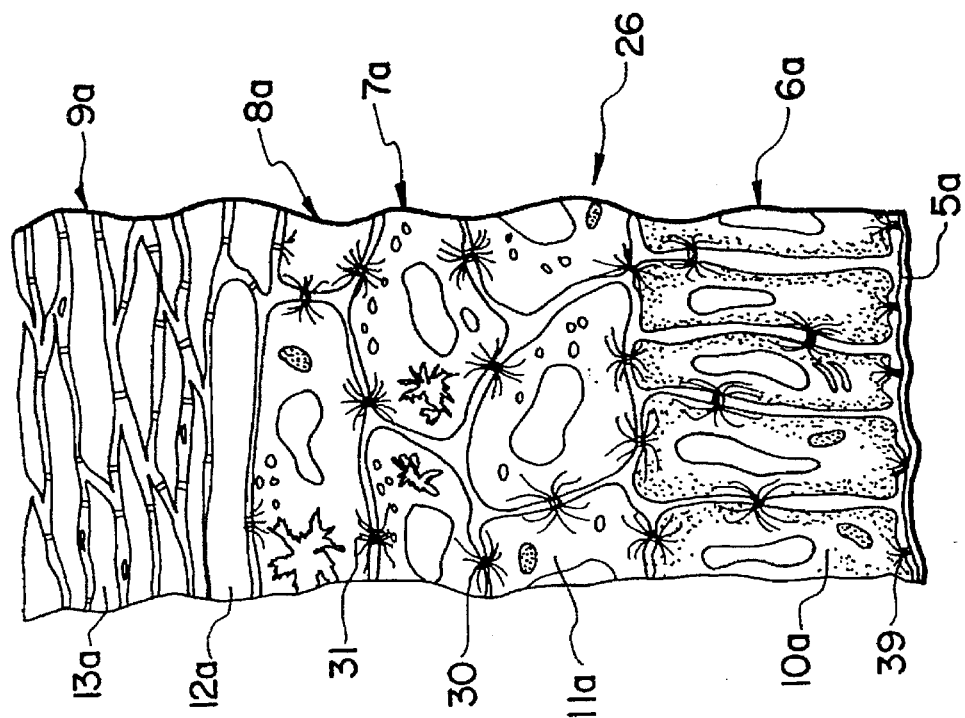
FIG. 5 is a partial section of the epidermis equivalent in a skin substitute, formed in accordance with the invention specifications.

Upon completion of the epidermis development phase of the process, the skin substitute (27) is obtained; FIG. 5 shows a partial section of the epidermis substitute (26). In accordance with procedures, this section has been made following staining with hemalun-phloxin-saffron.

The skin substitute (27) produced according to the process described above is, therefore, made up of a dermis substitute coverered with an epidermis substitute (26). The dermis equivalent is a film formed from a type I collagen gel containing fibroblasts arranged three-dimensionally in the film. The epidermis substitute (26) shown in FIG. 5 contains a basal membrane equivalent (5a), made up, in turn, of the depositing of a layer of laminine, fibronectin, type IV collagen, and the bubbly pemphigus antigen. Above the basal membrane equivalent are found keratinocytes (10a) in a palisade arrangement, attached to the membrane by hemidesmosomes (39): thus, a basal layer substitute is observed (6a). One may also observe cells that become progressively differentiated from the cells (10a) of the basal layer (6a) to the flat cells (13a) arranged near the free surface; desmosomes link together the cells of the various layers. The substitute corneous (9a), Malpighian (7a), and granular (8a) layers are very similar to the layers of real human skin.

Furthermore, the keratinocytes of the epidermis substitute (26) contain keratin fibers (31). It may be observed that the basic keratin, with a value of 67 kDa, which is an indicator of terminal differentiation usually absent in state-of-the-art cultures and in freshly-extracted hair follicles, is normally synthesized in the suprabasal layers (7a and 8a), as is the case for its complement, acidic keratin with a value of 56.5 kDa. In addition, the keratin 67 kDa is detected beginning in the suprabasal layer (7a), as in normal skin.

Filaggrine is also present in the epidermis equivalent (26), in the granular layer equivalent (8a). It is the result of the proteolytic maturation of its precursor, profilaggrine. Using electrophoresis, it may be observed that the filaggrine is appropriately cut at the level of the oligo-peptide bonds of the profilaggrine. The invention process allows, therefore, for the maturation of the profilaggrine in the human keratinocytes.

The skin substitute (26) thus formed is, therefore, well-differentiated and well-structured. It is also uniform in thickness and differentiation.

Lastly, adhesion of the dermis and epidermis substitutes is excellent, allowing easy handling of the skin substitute (27) formed in this way.

We claim:

1. A process for preparing a skin substitute comprising dermis substitute and epidermis substitute comprising the steps of:
   (a) preparing a dermis substitute by admixing
      i) contractile cells collected from unilayer cultures comprising a nutritive medium implanted with animal cutaneous tissue comprising dermis and epidermis and
      ii) a culture nutritive medium to which has been added native type I collagen as a component,
   said mixture forming a gel which contracts, thereby expelling nutritive medium and forming said dermis substitute;
   (b) preparing an epidermis substitute by employing said dermis substitute as a substrate by culturing said substrate with keratinocytes from an animal extracted sample and maintaining conditions promoting the proliferation of keratinocytes on the surface of said substrate,
   (c) promoting the growth of said culture of said substrate with said keratinocytes such that a skin substitute is produced by employing at least one nutritive medium maintained in contact with said keratinocytes,
   said substrate being implanted with at least one hair follicle or a section of a hair follicle extracted from animal skin, wherein said hair follicle or section of a hair follicle is obtained by cutting an extracted hair follicle perpendicularly to its median longitudinal line, in the area in which said hair follicle remains enclosed in the cellular sheath thereof so as to obtain a length of between approximately 0.5 and 5 mm,
   said follicle or follicle section retaining its cellular sheath and being implanted in said substrate in such a way that its median longitudinal line is substantially perpendicular to the surface of said substrate, and
   (d) extracting said hair follicle or section of a hair follicle from said dermis substitute at the end of approximately 8–13 days.

2. The process of claim 1 wherein said contractile cells are fibroblasts.

3. The process of claim 2 wherein said fibroblasts are normal fibroblasts obtained from human donors and collected from unilayer cultures by the process of trypsinization.

4. The process of claim 1 wherein said nutritive medium is Essential Minimum Medium.

5. The process of claim 1 wherein said culture nutritive medium to which have been added components of the extracellular matrix of the dermis is a medium containing at least collagen.

6. The process of claim 1 wherein said culture nutritive medium to which have been added components of the extracellular matrix of the dermis is a medium containing type I collagen.

7. The process of claim 6 wherein said dermis substitute prepared by
   (a) obtaining a slightly acidic collagen solution by soft acid extraction on an animal tissue,
   (b) mixing said solution obtained in (a), above, with said contractile cells and said nutritive medium,
   (c) neutralizing said mixture from (b), above, by the addition thereto of a basic salt,
   (d) pouring the neutralized mixture from (c), above, into a flat bottom container and
   (e) permitting the gel resulting from (d), above, to contract for several days.

8. The process of claim 7 wherein said nutritive medium comprises:
   (1) 80–100 volume percent Essential Minimum Medium,
   (2) 0–20 volume percent fetal calf serum,
   (3) 0–20 volume percent human AB group serum,
   (4) 0–1 weight percent anti-fungal agent,
   (5) 0–10 weight percent antibiotic,
   (6) 0–2 weight percent energizing compound, and
   (7) 0–2 weight percent non-essential amino acid.

9. The process of claim 1 wherein said hair follicle or section of a hair follicle is implanted in said substrate at a distance of from 0.1 to 2 mm, measured from the free surface of said substrate.

10. The process of claim 1 wherein said hair follicle or section of a hair follicle is cut near the base thereof so as to eliminate the bulb thereof.

11. The process of claim 1 wherein said hair follicle or section of a hair follicle is implanted in said substrate as soon as said substrate begins to contract.

12. The process of claim 1 wherein in step (c) the implanted hair follicle or section of a hair follicle is immersed in said nutritive medium for a period of time of approximately 3–6 days.

13. The process of claim 12 which includes at the expiration of said 5–6 day immersion period, replacing said nutritive medium with another nutritive medium, the level of said other nutritive medium being raised to a point within the thickness of said dermis substitute.

14. The process of claim 13 wherein said another nutritive medium comprises (1) 80–100 volume percent Essential Minimum Medium,
(2) 0–10 weight percent of at least one of an antibiotic and an anti-fungal agent and
(3) 0–0.5 weight percent of a growth factor.

15. The process of claim 1 wherein said skin substitute is continually maintained in contact with said nutritive medium subsequent to extraction of said implanted hair follicle or section of a hair follicle from said dermis substitute so as to allow keratinocytes developed on said dermis substrate to totally cover said dermis substrate and allow a significant degree of differentiation of the keratinocytes.

16. The process of claim 15 wherein a plurality of said hair follicle or section of a hair follicle is implanted evenly and spaced approximately 0.5 to 2.5 cm apart and said skin substitute after extraction therefrom of said plurality of hair follicle or section of a hair follicle is maintained in contact with said nutritive medium for a period of approximately 15 days to several months.

17. The process of claim 1 wherein said animal cutaneous tissue and said animal skin is human cutaneous tissue and human skin.

18. A process for preparing a skin substitute comprising dermis substitute and epidermis substitute comprising the steps of:
    (a) preparing a dermis substitute by admixing
        i) contractile cells collected from unilayer cultures comprising a nutritive medium implanted with animal cutaneous tissue comprising dermis and epidermis and
        ii) a culture nutritive medium to which has been added native type I collagen as a component,
    said mixture forming a gel which contracts, thereby expelling nutritive medium and forming said dermis substitute;
    (b) preparing an epidermis substitute by employing said dermis substitute as a substrate by culturing said substrate with keratinocytes from an animal extracted sample and maintaining conditions promoting the proliferation of keratinocytes on the surface of said substrate,
    (c) promoting the growth of said culture of said substrate with said keratinocytes such that a skin substitute is produced by employing at least one nutritive medium maintained in contact with said keratinocytes for a period of time of approximately 5–6 days,
    said substrate being implanted with at least one hair follicle or a section of a hair follicle extracted from animal skin,
    said follicle or follicle section retaining its cellular sheath and being implanted in said substrate in such a way that its median longitudinal line is substantially perpendicular to the surface of said substrate,
    (d) at the expiration of the 5–6 day immersion period, replacing said nutritive medium with another nutritive medium, the level of said another nutritive medium being raised to a point within the thickness of said dermis substitute,
    said dermis substitute being placed on a support grid raised from the bottom of said receptacle in order to ensure that said another nutritive medium reaches the desired level, and adjusting the level of said another nutritive medium so that said support grid is covered without, however, covering the upper surface of the skin substitute in its formative phase, and
    (e) extracting said hair follicle or section of a hair follicle from said dermis substrate at the end of approximately 8–13 days.

19. A process for preparing a skin substitute composed of a dermis equivalent covered with an epidermis equivalent, said dermis equivalent being a matrix formed from a type I collagen gel containing fibroblasts arranged three-dimensionally in said matrix, wherein said epidermis equivalent contains:
    (a) a basal membrane equivalent formed from the deposit of a layer of laminine, fibronectin and type IV collagen,
    (b) cells of the basal layer in a palisade arrangement, attached to the membrane equivalent according to paragraph (a) by hemidesmosomes and showing polar distribution of the bullous pemphigoid antigen;
    (c) cells of the suprabasal layers which, beginning with the first suprabasal layer, contain basic keratin with a value of 67 kDa, and acidic keratin with a value of 56.6 kDa;
    (d) granular cells containing involucrine, transglutaminase, filaggrine, keratohyaline granules and membrane coating granules, and
    (e) flat and keratinized cells arranged near the free surface, giving, after extraction using dodecyl sulfate and 2-mercaptoethanol, corneous envelopes characteristic of
    said follicle or fellicle section retaining its cellular sheath and being implanted in said substrate in such a way that its median longitudinal line is substantially perpendicular to the surface of said substrate.

20. A skin substitute comprising dermis substitute and epidermis substitute produced from the process comprising the steps of:
    (a) preparing a dermis substitute by admixing
        i) contractile cells collected from unilayer cultures comprising a nutritive medium implanted with animal cutaneous tissue comprising dermis and epidermis and
        ii) a culture nutritive medium to which has been added native type I collagen as a component,
    said mixture forming a gel which contracts, thereby expelling nutritive medium and forming said dermis substitute;
    (b) preparing an epidermis substitute by employing said dermis substitute as a substrate by culturing said substrate with keratinocytes from an animal extracted sample and maintaining conditions promoting the proliferation of keratinocytes on the surface of said substrate,
    (c) promoting the growth of said culture of said substrate with said keratinocytes such that a skin substitute is produced by employing at least one nutritive medium maintained in contact with said keratinocytes,
    said substrate being implanted with at least one hair follicle or a section of a hair follicle extracted from animal skin, wherein said hair follicle or section of a hair follicle is obtained by cutting an extracted hair follicle perpendicularly to its median longitudinal line, in the area in which said hair follicle remains enclosed in the cellular sheath thereof so as to obtain a length of between approximately 0.5 and 5 mm,
    said follicle or follicle section retaining its cellular sheath and being implanted in said substrate in such a way that its median longitudinal line is substantially perpendicular to the surface of said substrate, and
    (d) extracting said hair follicle or section of a hair follicle from said dermis substrate at the end of approximately 8–13 days.

21. A skin substitute comprising dermis substitute and epidermis substitute produced from the process comprising the steps of:

(a) preparing a dermis substitute by admixing
   i) contractile cells collected from unilayer cultures comprising a nutritive medium implanted with animal cutaneous tissue comprising dermis and epidermis and
   ii) a culture nutritive medium to which has been added native type I collagen as a component, said mixture forming a gel which contracts, thereby expelling nutritive medium and forming said dermis substitute;

(b) preparing an epidermis substitute by employing said dermis substitute as a substrate by culturing said substrate with keratinocytes from an animal extracted sample and maintaining conditions promoting the proliferation of keratinocytes on the surface of said substrate, (c) promoting the growth of said culture of said substrate with said keratinocytes such that a skin substitute is produced by employing at least one nutritive medium maintained in contact with said keratinocytes for a period of time of approximately 5–6 days, said substrate being implanted with at least one hair follicle or a section of a hair follicle extracted from animal skin, said follicle or follicle section retaining its cellular sheath and being implanted in said substrate in such a way that its median longitudinal line is substantially perpendicular to the surface of said substrate, (d) at the expiration of the 5–6 day immersion period, replacing said nutritive medium with another nutritive medium, the level of said other nutritive medium being raised to a point within the thickness of said dermis substitute, said dermis substitute being placed on a support grid raised from the bottom of said receptacle in order to ensure that said another nutritive medium reaches the desired level, and adjusting the level of said another nutritive medium so that said support grid is covered without, however, covering the upper surface of the skin substitute in its formative phase, and (e) extracting said hair follicle or section of a hair follicle from said dermis substrate at the end of approximately 8–13 days.

* * * * *